US010801033B2

(12) United States Patent
Gupta et al.

(10) Patent No.: US 10,801,033 B2
(45) Date of Patent: Oct. 13, 2020

(54) RECOMBINANT POLYNUCLEOTIDE INVOLVED IN LACTONE SYNTHESIS AND PROCESS FOR SYNTHESIS OF LACTONES THEREOF

(71) Applicant: Council of Scientific & Industrial Research, New Delhi (IN)

(72) Inventors: Vidya Shrikant Gupta, Pune (IN); Ashish Balwant Deshpande, Pune (IN); Pranjali Sudhir Oak, Pune (IN); Ashok Prabhakar Giri, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 76 days.

(21) Appl. No.: 16/091,229

(22) PCT Filed: Apr. 4, 2017

(86) PCT No.: PCT/IN2017/050128
§ 371 (c)(1),
(2) Date: Oct. 4, 2018

(87) PCT Pub. No.: WO2017/175241
PCT Pub. Date: Oct. 12, 2017

(65) Prior Publication Data
US 2019/0153459 A1 May 23, 2019

(30) Foreign Application Priority Data
Apr. 5, 2016 (IN) .............................. 201611011975

(51) Int. Cl.
*C12N 15/82* (2006.01)
*C12N 9/08* (2006.01)
*C12N 9/14* (2006.01)

(52) U.S. Cl.
CPC ....... *C12N 15/8243* (2013.01); *C12N 9/0065* (2013.01); *C12N 9/14* (2013.01); *C12Y 301/03076* (2013.01)

(58) Field of Classification Search
CPC ..... C12N 9/14; C12N 9/0065; C12N 15/8243
See application file for complete search history.

(56) References Cited

FOREIGN PATENT DOCUMENTS

WO 2010035154 A1 4/2010

OTHER PUBLICATIONS

Huang, Fong-Chin, and Wilfried Schwab. "Overexpression of hydroperoxide lyase, peroxygenase and epoxide hydrolase in tobacco for the biotechnological production of flavours and polymer precursors." Plant biotechnology journal 10.9 (2012): 1099-1109. (Year: 2012).*

GenBank Accession KX090179.1 for MiEH2; Mar. 26, 2017. (Year: 2017).*
GenBank Accession CM021843.1 for Chromosome 7 from Mangifera indica 'Alfonso' Mar. 10, 2020. (Year: 2020).*
Genbank Accession KX090185.1 for PGX1; Mar. 26, 2017. (Year: 2017).*
Abbott Chalew et al., "Evaluation Nanoparticle Breakthrough during Drinking Water Treatment", Environmental Health Perspectives, vol. 121, No. 10, 2013, pp. 1161-1166.
Calatrava, "Mango: Economics and International Trade", Institute for Agricultural Research, Department of Agricultural Economics, Granada, Spain; Apr. 1, 2014, XP55410377, URL:https://www.researchgate.net/profile/Javier_Calarava-Requena2/publication/261634596_Mango_Economics_and_International_Trade/links/54ab30e00cf2ce2df668dabe/Mango-Economics-and-International-Trade.pdf?origin=publication_detail [retrieved from the Internet on Sep. 27, 2017]; pp. 1-46.
Cardillo et al., "On the Mode of Conversion of Racemic, C14-C19, y-Hydroxy Alkene Fatty Acids into C7-C11, Dptically Active y- and o-Lactones in Cladosporium suaveolense", Journal of Organic Chemicstry, vol. 54, 1989, pp. 4979-4980.
Chidley et al., "Spatial and temporal changes in the volatile profile of Alphonso mango upon exogenous ethylene treatment", Food Chemistry, vol. 136 2013, pp. 585-594.
Deshpande et al., "Isolation and characterization of 9-lipoxygenase and epoxide hydrolase 2 genes: Insight into lactone biosynthesis in mango fruit (*Mangifera indica* L.)", Phytochemistry, vol. 138, pp. 65-75.
Haffner et al., "174. Biosynthesis of o-Jasmin Lactone (= (Z)-Dec-7-eno-5-lactone) and (Z,Z)-Dodeca-6,9-dieno-4-lactone in the Yeast *Sporobolomyces odorus*", Helvetica Chimica Acta, vol. 79, 1996, pp. 2088-2099.
Haffner et al., "Stereospecific Metabolism of Isomeric Epoxyoctadecanoic acids in the Lactone-Producing Yeast *Sporidiobolus salmonicolor*" Lipids, vol. 33, No. 1, 1998, pp. 47-58.
Huang et al., "Overexpression of hydroperoxide lyase, peroxygenase and epoxide hydrolase in tobacco for the biotechnological production of flavours and polymer precursors", Plant Biotechnology Journal, vol. 10, 2012, pp. 1099-1109.
Huang et al., "Molecular characterization of NbEH1 and NbEH2, two epoxide hydrolases from Nicotiana benthamiana", Phytochemistry, vol. 90, 2013, pp. 6-15.
Idstein et al., "Volatile Constituents of Alphonso Mango (*Mangifera indica*)", Phytochemistry, vol. 24, No. 10, 1985, pp. 2313-2316.

(Continued)

*Primary Examiner* — Russell Kallis
(74) *Attorney, Agent, or Firm* — Dinsmore & Shohl LLP

(57) ABSTRACT

The present invention provides the polynucleotide encoding enzyme involved in lactone synthesis and a process for synthesis of lactones using said polynucleotides. The invention also provides recombinant plasmid expression vector comprising said polynucleotide sequence. The recombinant protein encoded by said polynucleotides leads to synthesis of lactones having flavour peculiar to Alphonso mangoes.

9 Claims, 4 Drawing Sheets
Specification includes a Sequence Listing.

(56) References Cited

OTHER PUBLICATIONS

Kapila et al., "An Agrobacterium-mediated transient gene expression system for intact leaves", Plant Science, vol. 122, 1997, pp. 101-108.

Koncz et al., "The promoter of TL-DNA gene 5 controls the tissue-specific expression of chimaeric genes carried by a novel type of Agrobacterium binary vector", Mol Gen Genet, vol. 204, 1986, pp. 383-396.

Kulkarni et al., "Geographic variation in the flavour volatiles of Alphonso mango", Food Chemistry, vol. 130, 2012, pp. 58-66.

Pandit et al., "Cultivar relationships in mango based on fruit volatile profiles", Food Chemistry, vol. 114, 2009, pp. 363-372.

Pandit et al., Changes in volatile composition during fruit development and ripening of 'Alphonso' mango, J Sci Food Agric, vol. 89, 2009, pp. 2071-2081.

Sánchez et al., "An integrative "omics" approach identifies new candidate genes to impact aroma volatiles in peach fruit", BMC Genomics, vol. 14:343, 2013, pp. 1-23.

Schóttler et al., "125. Biosynthesis of Dodecano-4-lactone in Ripening Fruits: Crucial Role of an Epoxide-Hydrolase in Enantioselective Generation of Aroma Components of the Nectarine (*Prunus persica* var. *nucipersica*) and the Strawberry (*Fragaria ananassa*)", vol. 79, 1996, pp. 1488-1496.

Spolaore et al., "A simple protocol for transient gene expression in ripe fleshy fruit mediated by Agrobacterium", Journal of Experimental Botany, vol. 52, No. 357, 2001, pp. 845-850.

Tuynenburg et al., "Microbiology, Muller's Phenomenon", Nature, vol. 194, 1962, pp. 995-996.

Vecchietti et al., "Comparative analysis of expressed sequence tags from tissues in ripening stages of peach (*Prunus persica* L. *batsch*)", Tree Genetics & Genomes, vol. 5:377, 2009, pp. 377-391.

Wijekoon et al., "The involvement of two epoxide hydrolase genes, NbEH1.1 and NbEH1.2, of Nicotiana benthamiana in the interaction with Colletotrichum destructivum, Colletotrichum orbiculare or *Pseudomonas syringae* pv. *tabaci*", Functional Plant Biology, vol. 35, 2008, pp. 1112-1122.

Wilson et al., "Importance of Some Lactones and 2,5-Dimethyl-4-hydroxy-3(2H)-furanone to Mango (*Mangifera indica* L.) Aroma", J. Agric. Food Chem., vol. 38, 1990, pp. 1556-1559.

International Search Report (Re-Issued) and Written Opinion completed Sep. 27, 2017, pertaining to PCT/IN2017/050128.

\* cited by examiner (a)

(b)

RECOMBINANT POLYNUCLEOTIDE INVOLVED IN LACTONE SYNTHESIS AND PROCESS FOR SYNTHESIS OF LACTONES THEREOF

FIELD OF THE INVENTION

The present invention relates to nucleotide sequences encoding enzymes in the lactone synthesis pathway, the cloning, and expression of the said sequences, as well as recombinant constructs comprising said sequences. More particularly, the present invention relates to nucleotide sequences encoding epoxide hydrolase 2 and a nucleotide sequence encoding peroxygenase.

BACKGROUND OF THE INVENTION

Consumption of various foods is based on one's organoleptic perception. Organoleptic perception is the impression of taste, texture, visual appearance and aroma of food. The collective olfaction of taste and aroma through retronasal and orthonasal receptors determine food flavour. It is a known fact that aromatic compounds contribute a major share to food flavour. Several aroma related studies have been carried on fruits as they possess diversity in their flavour profile accompanied with unique aroma. These studies have revealed a blend of volatile compounds present in fruits to be responsible for this unique aroma.

Analysis of mango (*Mangifera indica* L.) has shown presence of various volatile compounds viz. alkanes, alkenes, aldehydes, alcohols, monoterpenes, sesquiterpenes, oxygenated monoterpenes, oxygenated sesquiterpenes, non-terpene hydrocarbons, furanones and lactones (Pandit et al. 2009b). Alphonso, as one of the most favored and exported Indian mango cultivar shows qualitative volatile abundance among the 22 Indian and 5 exotic mango cultivars (Pandit et al. 2009a). Among all groups of volatile compounds, lactones and furanones are important due to their specific ripening appearance in mango. Interestingly, 14 different lactones have been reported from Alphonso, which is the highest number of lactones known from any single fruit (Idstein and Schreier 1985; Wilson et al. 1990).

Structurally, lactones are cyclic esters characterized by a closed ring consisting of four or five carbon atoms and a single oxygen atom, with a ketone group (C=O) in one of the carbons adjacent to the oxygen in ring. Although lactones exhibit qualitative abundance, they are present at lower concentrations in Alphonso. However, they pose a high impact on overall Alphonso flavour due to their lower odor detection threshold (Kulkarni et al. 2012). Further lactones are known to impart sweet fruity flavour which is the characteristic feature of fully ripe fruit (Wilson et al. 1990). Thus lactones can be considered as marker metabolites of Alphonso ripening. Despite structural and functional characterization of these vital flavour metabolites the pathway of their biosynthesis is still left unidentified.

Even though earlier attempts to identify probable precursors of lactone biosynthesis have been made, a specific pathway indicating lactone biosynthesis in mango has not been identified. Studies on different yeasts, molds and bacteria suggested fatty acids and keto acids to be the origin of lactone biosynthesis. Upon microbial reduction, synthesized hydroxy fatty acids can be converted to lactones by simple heating (Tuynenburg. G et al. 1962). Deuterium labelling studies on yeast (*Sporobolomyces odorus*) suggested involvement of unsaturated fatty acids as precursors for δ-Jasmin lactone (Haffner et al. 1996). Additionally, Haffner and Tressl (1998) proposed epoxy fatty acid metabolism by epoxide hydrolase (EH) for gamma lactone production in *Sporidiobolus salmonicolor* through deuterium labelling studies. Further, a study on nectarines by Schottler and Boland (1996) showed that on administration of $^{18}O$ labelled all three mono-epoxides of linolenic acid (9-10 epoxy/12-13 epoxy/15-16 epoxy linolenic acid) produced dodeca-6, 9-dieno-4-lactone and hexano-4-lactone, therefore suggesting possible epoxy fatty acid involvement in lactone production by EH activity. This finding was also supported by comparative ESTs analysis from ripening *Prunus persica* L. Batsch, wherein analysis revealed EH as a key gene responsible for lactone production (Vecchietti et al. 2009). It is known that epoxy fatty acid synthesis in plants is carried out by peroxygenase (PGX) activity. Plant PGX is known to utilize lipoxygenase (LOX) products viz. hydroperoxy-dienoic (HOPD) and hydroperoxy-trienoic (HOPT) acids as co-substrates producing their respective monohydroxy fatty acid. Monohydroxy and epoxy fatty acids thus produced can be precursors for lactone biosynthesis.

PCT Publication No. WO2010035154 relating to recombinant proteins of epoxide hydrolase (EH) from peach reports three different nucleotide sequences responsible for lactone production in peach. However, the lactones in peach and mango vary considerably thereby conferring a varied flavour to fruits.

These initial efforts to understand lactone biosynthesis from microorganisms and plants have insinuated involvement of PGX and EH genes and their corresponding enzymes in lactone biosynthesis. However, there have been no attempts in prior art to obtain increased lactone production in mangoes using enzymes known to be precursors for lactone biosynthesis.

In view of the lack of knowledge of the mechanism of enzymes in lactone biosynthesis in mangoes, there is a need in the art to isolate, and conduct molecular and biochemical characterization of nucleotide sequences encoding enzymes such as epoxide hydrolase 2 (EH2) and peroxygenase (PGX).

OBJECTS OF THE INVENTION

An object of the present invention is to provide a nucleotide sequence encoding a recombinant polypeptide involved in lactone synthesis, and overexpressing the said sequences in host cells to obtain increased lactone production.

Another object of the present invention is to provide for the production of volatile compounds such as lactones in mangoes, wherein enzymes involved in the synthesis of the said compounds are encoded by cDNA nucleotide sequences synthesized by the present inventors.

SUMMARY OF THE INVENTION

Accordingly, the present invention provides a polynucleotide for lactone biosynthesis, wherein the polynucleotide is selected from the group comprising:
(a) a polynucleotide sequence as set forth in SEQ ID No. 1 encoding a recombinant polypeptide epoxide hydrolase 2 of SEQ ID No. 3; and
(b) a polynucleotide sequence as set forth in SEQ ID No. 4 encoding a recombinant polypeptide peroxygenase of SEQ ID No. 6.

In an aspect of the invention, the polynucleotide is a cDNA.

In another aspect of the invention the polynucleotide encoding epoxide hydrolase 2 consisting of SEQ ID No. 1 catalyzes the conversion of epoxy fatty acids to di-hydroxy fatty acids and the polynucleotide sequence encoding peroxygenase consisting of SEQ ID No. 4 catalyzes the conversion of unsaturated fatty acids to epoxy fatty acids.

In still another aspect of the invention, there is provided a process for synthesis of lactones said process comprising:
(a) synthesizing polynucleotide sequence as set forth in SEQ ID No.: 4;
(b) expressing a recombinant construct carrying said polynucleotide sequence of SEQ ID No. 4 in a host cell to obtain recombinant polypeptide peroxygenase of SEQ ID No. 6;
(c) catalyzing conversion of unsaturated fatty acids to epoxy fatty acids in presence of the recombinant polypeptide peroxygenase of SEQ ID No. 6 of step (b) to obtain epoxy fatty acids;
(d) synthesizing polynucleotide sequence as set forth in SEQ ID No.: 1;
(e) expressing a recombinant construct carrying said polynucleotide sequence of SEQ ID No. 1 in a host cell to obtain recombinant polypeptide peroxygenase of SEQ ID No. 3;
(f) catalyzing conversion of the epoxy fatty acids from step (c) to di-hydroxy fatty acids in presence of the recombinant polypeptide peroxygenase of SEQ ID No. 3 of step (e) to obtain di-hydroxy fatty acids; and
(g) subjecting the di-hydroxy fatty acids of step (f) to multiple cycles of ω and β oxidation to obtain the lactones.

Di-hydroxy fatty acids and epoxy fatty acids are intermediary compounds in lactones synthesis. Peroxygenase from *M. indica* produces epoxy fatty acids from unsaturated fatty acids eg. Linoleic acid (LA), α-linolenic acid (ALA), etc., followed by MiEH2 converting epoxy fatty acids to dihydroxy fatty acids. Hydroperoxy fatty acids and hydroxy fatty acids are identified to be precursors for lactone biosynthesis (Haffner and Tressl 1998; Cardillo et al. 1989). The di-hydroxy fatty acid obtained from epoxy fatty acids in presence of epoxide hydrolase 2 undergoes multiple cycles of alpha and beta oxidation to obtain lactones. The present invention provides synthetic, full length polynucleotide sequences encoding enzymes important in lactone production and their subsequent transient expression in mangoes.

In a further aspect the present invention provides primers for amplification and synthesis of full-length nucleotide sequences. Accordingly, the primer sequences are selected from the group consisting of nucleotide sequences selected from SEQ ID No. 7 to 12 for synthesis of SEQ ID No. 1. For synthesis of SEQ ID No. 4, primers are selected from the group consisting of SEQ ID No. 19 to 24.

In yet another aspect, the present invention provides a recombinant vector construct comprising cDNA nucleotide sequences selected from SEQ ID No. 1 and SEQ ID No. 4 cloned into plasmid vectors selected from the group consisting of cloning vector pGEMT, bacterial expression vector pEXP5-CT/TOPO and plant expression vector pBI121.

The said vector construct carrying the polynucleotide sequence is transformed in host cells to achieve transient expression. Accordingly, transient expression of a recombinant construct comprising a cloning vector carrying nucleotide sequence selected from SEQ ID No. 1 and SEQ ID No. 4 is achieved by transformation of the said recombinant constructs in *Agrobacterium* and consequent overexpression of the said transcripts in ripe fruits such as mangoes.

In one more aspect, the present invention provides a process for synthesis of lactones having flavour peculiar to Alphonso mangoes, said process comprising:
(a) synthesizing polynucleotide sequence as set forth in SEQ ID No.: 4;
(b) expressing a recombinant construct carrying said polynucleotide sequence of SEQ ID No. 4 in a host cell to obtain recombinant polypeptide peroxygenase of SEQ ID No. 6;
(c) catalyzing conversion of unsaturated fatty acids to epoxy fatty acids in presence of the recombinant polypeptide peroxygenase of SEQ ID No. 6 of step (b) to obtain epoxy fatty acids;
(d) synthesizing polynucleotide sequence as set forth in SEQ ID No.: 1;
(e) expressing a recombinant construct carrying said polynucleotide sequence of SEQ ID No. 1 in a host cell to obtain recombinant polypeptide peroxygenase of SEQ ID No. 3;
(f) catalyzing conversion of the epoxy fatty acids from step (c) to di-hydroxy fatty acids in presence of the recombinant polypeptide peroxygenase of SEQ ID No. 3 of step (e) to obtain di-hydroxy fatty acids; and
(g) subjecting the di-hydroxy fatty acids of step (f) to multiple cycles of ω and β oxidation to obtain the lactones.

BRIEF DESCRIPTION OF ACCOMPANYING DRAWINGS

FIG. 1 depicts the CBB stained SDS-PAGE gels representing purified recombinant protein MiEH2;

FIG. 2 indicates agroinfiltration of empty pBI121 and pBI121 comprising nucleotide sequences selected from SEQ ID No. 1/SEQ ID No. 4 constructs in two different regions of the same mango fruit separated by fruit stone (a). Representative images of Alphonso mango fruit after agroinfiltration and Gus staining (b).

FIG. 3 represents extracted ion chromatograms from HRMS analysis for product identification of MiEH2 assay reactions, standards; TSO (a), meso hydrobenzoin (b), CSO (d), R, R (+) hydrobenzoin (e), 12,13 EpOME (g). Chromatogram representing product formation by MiEH2 with substrates TSO (c), CSO (f) and 12,13 EpOME (h). Assay reaction of protein expressed from empty vector with 12,13 EpOME substrate (i). X axes represents retention time (min) and Y axes represents relative intensity;

Figure 6:
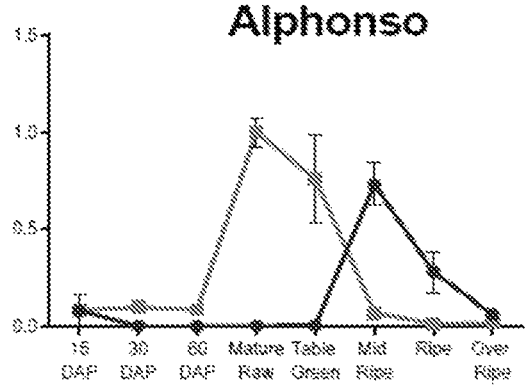
Figure 6:
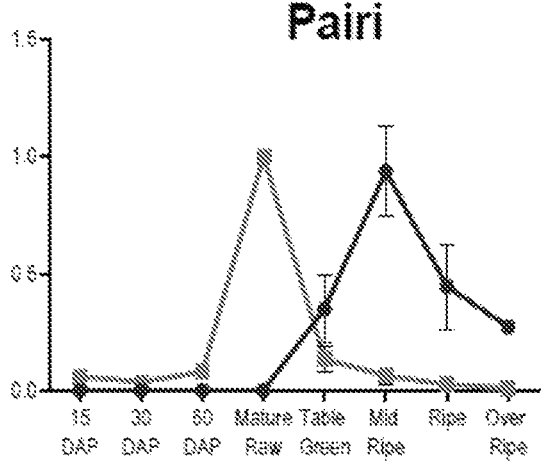
Figure 6:
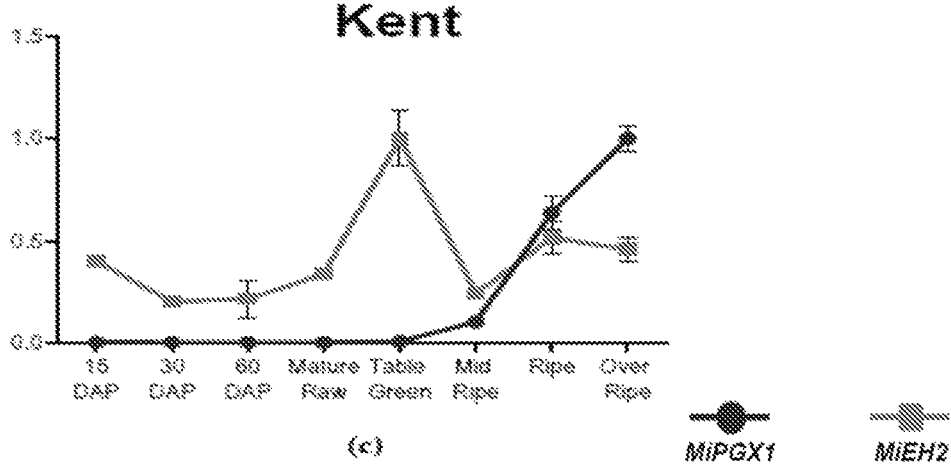

FIG. 6 depicts transcript profiles of MiPGX1 and MiEH2 from pulp and skin tissues of various fruit development and ripening stages of Alphonso (a), Pairi (b) and Kent (c) mango cultivars. Vertical bars at each data point represent standard error in the relative quantification among the biological replicates. X axes represents fruit development and ripening stages and Y axes represents relative transcript abundance.

BRIEF DESCRIPTION OF SEQUENCE LISTING

SEQ ID No. 1 represents polynucleotide encoding polypeptide epoxide hydrolase 2 (957 bp)

SEQ ID No. 2 represents nucleotide sequence encoding epoxide hydrolase 2 (1875 bp)
SEQ ID No. 3 represents amino acid sequence of epoxide hydrolase 2 (318 bp)
SEQ ID No. 4 represents polynucleotide encoding polypeptide peroxygenase (708 bp)
SEQ ID No. 5 represents nucleotide sequence encoding peroxygenase (1515 bp)
SEQ ID No. 6 represents amino acid sequence of peroxygenase (235 bp)
SEQ ID No. 7 represents forward primer EH DeF1 (17 bp)
SEQ ID No. 8 represents reverse primer EH DeR4 (14 bp)
SEQ ID No. 9 represents forward primer EHRCF2 (22 bp)
SEQ ID No. 10 represents reverse primer EHRCR1 (22 bp)
SEQ ID No. 11 represents forward primer EHtrF1 (27 bp)
SEQ ID No. 12 represents reverse primer EHtrR1 (28 bp)
SEQ ID No. 13 represents forward primer EHTOPO_F1 (24 bp)
SEQ ID No. 14 represents reverse primer EHTOPO_R1 (14 bp)
SEQ ID No. 15 represents forward primer EHpBI121F1 (39 bp)
SEQ ID No. 16 represents reverse primer EHpBI121R1 (43 bp)
SEQ ID No. 17 represents forward primer EHRTF4 (25 bp)
SEQ ID No. 18 represents reverse primer EHRTR4 (25 bp)
SEQ ID No. 19 represents forward primer PGX_De_F (22 bp)
SEQ ID No. 20 represents reverse primer PGX_De_R (19 bp)
SEQ ID No. 21 represents forward primer PGX_RC_F (23 bp)
SEQ ID No. 22 represents reverse primer PGX_RC_R (22 bp)
SEQ ID No. 23 represents forward primer MiPGX_Tr_F (24 bp)
SEQ ID No. 24 represents reverse primer MiPGX_Tr_R (27 bp)
SEQ ID No. 25 represents forward primer MiPGX1_RT_F1 (25 bp)
SEQ ID No. 26 represents reverse primer MiPGX1_RT_R1 (25 bp)

DETAILED DESCRIPTION OF THE INVENTION

The invention will now be described in detail in connection with certain preferred and optional embodiments, so that various aspects thereof may be more fully understood and appreciated.

Alphonso, Pairi, and Kent varieties of mangoes used in the present invention were obtained from locations in Maharashtra, India. Alphonso and Pairi cultivars were collected from the Mango Research Sub Centre of Dr. Balasaheb Sawant Konkan Agricultural University, Dapoli, Deogad. cv. Kent vrieties were collected from the Regional Fruit Research Station, Dr. Balasaheb Sawant Konkan Agricultural University, Vengurle.

Plasmid vectors were commercially obtained/purchased; the cloning vector-pGEMT was procured from Promega, WI, USA; the bacterial expression vector pEXP5-CT/TOPO was procured from Invitrogen, Carlsbad, Calif., USA; and the plant expression vector pBI121 was procured from Clontech, Palo, Alto, Calif. NCBI Accession No. AF485783. The host cell BL21(DE3) pLysS Rosetta cells used for recombinant protein expression were obtained from Novagen, Madison, Wis., USA. E. coli (Top 10) cells were obtained from Novagen, Madison, Wis., USA. *Agrobacterium* strain GV3101 is employed as referred to by Koncz and Schell, 1986.

Epoxide hydrolase (EH) genes are categorized into two classes EH1 and EH2, EH1 catalyzes aromatic epoxide hydrolysis and EH2 catalyzes hydrolysis of fatty acids epoxides and aromatic compounds (Wijekoon et al. 2008; Huang and Schwab 2013). EH2 is known for its activity on epoxy fatty acids formed by peroxygenase to form hydroxy fatty acids. Hydroxy fatty acids formed undergo multiple cycles of α and β oxidation to obtain lactones such as aromatic alcohols. The lactone biosynthetic pathway is found to be functional in mangoes. Therefore, the polynucleotide sequences encoding epoxide hydrolase 2 and peroxygenase have been synthesized, cloned and expressed for their involvement in lactone synthesis.

In a preferred embodiment, the present invention provides a polynucleotide sequence encoding epoxide hydrolase 2 (EH2) represented by SEQ ID No. 1, wherein epoxide hydrolase 2 catalyzes conversion of epoxy fatty acids to di-hydroxy fatty acids.

In accordance with this embodiment, the present invention provides SEQ ID No. 1 consisting of a 957 base pair (bp) long nucleotide sequence encoding epoxide hydrolase 2 polypeptide of *Mangifera indica* as represented in SEQ ID No. 3.

The obtained SEQ ID No. 1 upon in silico analysis comprises a complete ORF of EH2 spanning 957 nucleotides with 74 nucleotides long 5' and 241 nucleotides long 3' UTR regions as represented in SEQ ID No. 1. Homology analysis indicate SEQ ID No. 1 encoding EH to have less than 75% sequence identity with other genes encoding plant soluble EH2 (Table 2).

In an embodiment, the present invention provides synthesis of SEQ ID No. 1 using primers comprising SEQ ID No. 7 to 12.

In another preferred embodiment, the present invention provides a recombinant vector construct comprising nucleotide sequence comprising SEQ ID No. 1 cloned into plasmid vectors selected from the group consisting of pGEMT, a bacterial expression vector (pEXP5-CT/TOPO) and a plant expression vector (pBI121) followed by transformation in host cells for expression.

Most preferably, the present invention provides transient expression of recombinant vector construct pBI121 carrying SEQ ID No. 1 to obtain increased lactone production in mangoes. The full length sequence of MiEH2, i.e. SEQ ID No. 1 was cloned in a pBI121 plant expression vector between CaMV 35S promoter and GusA gene. Terminal primers were designed (Table 1A) to clone genes at BamHI restriction site. The resulted correct oriented construct pBI121+SEQ ID No. 1 was transformed in the *Agrobacterium* GV3101 strain for transient expression. Over expression of EH2 was carried out by *Agrobacterium* mediated infiltration in ethylene treated mango fruits at 3DAH stage by using hypodermic syringe. Equal volumes of the said constructs i.e. pBI121+ MiEH2 and pBI121 empty vector construct were used for infiltration in two different halves of same mango fruit separated by fruit stone.

The present invention provides transient expression of SEQ ID No. 1 in a plant expression vector carrying the said SEQ ID No. 1 which transformed in an *Agrobacterium* strain and introduced in mangoes via agroinfiltration resulting in a significant overexpression of lactones selected from the group consisting of δ-valerolactone, γ-hexalactone and δ-hexalactone. A corresponding increase of 1.46, 1.96 and 1.98 fold more of δ-valerolactone, γ-hexalactone and δ-hexalactone was observed, respectively compared to control tissue.

In another preferred embodiment, the present invention provides a nucleotide sequence encoding peroxygenase of SEQ ID No. 4, wherein peroxygenase (upstream enzyme to epoxide hydrolase) catalyzes conversion of unsaturated fatty acids to epoxy fatty acids.

Accordingly, SEQ ID No. 4 comprises a nucleotide sequence spanning 708 bp encoding a peroxygenase polypeptide of *Mangifera indica* as represented in SEQ ID No. 6.

In a further embodiment, the present invention provides the synthesis of SEQ ID No. 4 using primers comprising SEQ ID No. 19 to 24.

In one more embodiment, the present invention provides transient expression of a plant expression vector carrying SEQ ID No. 4 which when transformed in an *Agrobacterium* strain and introduced in mangoes via agroinfiltration results in overexpression of transcripts encoding peroxygenase.

In one more preferred embodiment, the present invention provides a process for synthesis of lactones having flavour peculiar to Alphonso mangoes, said process comprising:
(a) synthesizing polynucleotide sequence as set forth in SEQ ID No.: 4;
(b) expressing a recombinant construct carrying said polynucleotide sequence of SEQ ID No. 4 in a host cell to obtain recombinant polypeptide peroxygenase of SEQ ID No. 6;
(c) catalyzing conversion of unsaturated fatty acids to epoxy fatty acids in presence of the recombinant polypeptide peroxygenase of SEQ ID No. 6 of step (b) to obtain epoxy fatty acids;
(d) synthesizing polynucleotide sequence as set forth in SEQ ID No.: 1;
(e) expressing a recombinant construct carrying said polynucleotide sequence of SEQ ID No. 1 in a host cell to obtain recombinant polypeptide peroxygenase of SEQ ID No. 3;
(f) catalyzing conversion of the epoxy fatty acids from step (c) to di-hydroxy fatty acids in presence of the recombinant polypeptide peroxygenase of SEQ ID No. 3 of step (e) to obtain di-hydroxy fatty acids; and
(g) subjecting the di-hydroxy fatty acids of step (f) to multiple cycles of ω and β oxidation to obtain the lactones.

In yet another embodiment of the present invention, the polynucleotide of SEQ ID No. 4 is synthesized by using primer pairs selected from the group consisting of SEQ ID No.: 19-SEQ ID No. 20, SEQ ID No.: 21-SEQ ID No. 22, SEQ ID No.: 23-SEQ ID No. 24, and SEQ ID No.: 25-SEQ ID No. 26.

A further embodiment of the present invention provides that the polynucleotide of SEQ ID No. 1 is synthesized by using primer pairs selected from the group consisting of SEQ ID No.: 7-SEQ ID No. 8, SEQ ID No.: 9-SEQ ID No. 10, SEQ ID No.: 11-SEQ ID No. 12, SEQ ID No.: 13-SEQ ID No. 14, SEQ ID No.: 15-SEQ ID No. 16, and SEQ ID No.: 17-SEQ ID No. 18.

Yet another embodiment of the present invention provides a method of enhancing the synthesis of lactone in fruit of a plant, wherein the method comprises introducing the plasmid expression vector comprising SEQ ID No. 1 or SEQ ID No. 4 in fruit of a plant by agroinfiltration, In a further embodiment of the present invention the plant in the process of agroinfiltration is mango.

The unsaturated fatty acids are selected from the group consisting of Linoleic acid (LA), α-linolenic acid (ALA). The epoxide of linoleic acid is 12,13-cis epoxide of linoleic acid (12,13 EpOME). The process of the present invention yields 8 lactones selected from the group consisting of γ-butyrolactone, δ-valerolactone, γ-hexalactone, δ-hexalactone, γ-octalactone, δ-octalactone, γ-decalactone and δ-decalactone. The different lactones were detected from all the tissues by GC-MS analysis as showed in FIG. 4. The recombinant vector and the host cell employed in the present process have been referred to in the description herein above. In case of transient expression of SEQ ID No. 1, over expression significantly increased contents of δ-valerolactone, γ-hexalactone and δ-hexalactone, this increase was 1.46, 1.96 and 1.98 folds more, respectively.

EXAMPLES

Following examples are given by way of illustration therefore should not be construed to limit the scope of the invention.

Example 1

Plant Sources

Plant material employed in the present invention was based on plant varieties. These varieties included cv. Alphonso and cv. Pairi which were collected from the Mango Research Sub Centre of Dr. Balasaheb Sawant Konkan Agricultural University, Dapoli, Deogad (Maharashtra, India, 16° 31' N, 73° 20' E). Fruits of cv. Kent were collected from the Regional Fruit Research Station, Dr. Balasaheb Sawant Konkan Agricultural University, Vengurle (Maharashtra, India, 15° 51' N, 73° 39' E). Four developing and four ripening stages of all three mango cultivars were collected. Developing stages were collected at 15 Days after Pollination (DAP), 30 DAP, 60 DAP and Mature raw stage (90DAP for cv. Alphonso and Pairi, 110DAP for cv. Kent). Fruits at these developing stages were harvested pulp(mesocarp) and skin(exocarp) were separated immediately. The tissues were snap frozen in liquid nitrogen and stored at −80° C. till further use.

Example 2

Pre-Treatment of Mangoes

A set of 12 fruits each for all the three cultivars, i.e. Alphonso, Pairi and Kent were harvested at their respective mature raw stage and stored in the hay containing boxes at ambient temperature for ripening. Since the three cultivars showed variation in the ripening duration, tissue for ripening stages were collected at Table Green, Mid Ripe, Ripe and Over Ripe stage (each stage is represented by days after harvest for cv. Alphonso as 5, 10, 15 and 20 days; for cv. Pairi as 4, 6, 8 and 10 days and for cv. Kent as 5, 8, 10 and 13 days respectively) based on the skin colour, aroma and fruit softness. At each ripening stage, fruits for each cultivar were removed from the storage boxes, followed by pulp and skin separation. The pulp and skin removed were frozen in liquid nitrogen and stored at −80° C. till further use. For transient expression studies ethylene treated fruits were collected as described by Chidley et al. (2013).

Example 3

RNA Isolation and cDNA Synthesis

Total RNA isolation was carried out for all the tissues sampled for current study using RNeasy Plus mini kit (Quiagen, Venlo, Netherlands). Two microgram of total RNA was used to carry out reverse transcription for synthesis of cDNA using High Capacity cDNA reverse transcription kit (Applied Biosystem, CA, USA).

Example 4

Isolation of Epoxide Hydrolase 2 cDNA

Isolation of partial gene sequence of EH2 from Alphonso mango was initiated by designing degenerate primers by the homology based approach. Nucleotide sequences of EH2 from other plant species retrieved from NCBI were aligned and degenerate primers EH DeF1, EH DeR4 (Table 1A) were designed. Amplification was carried out using cDNA prepared from ripe fruit as the template. The resultant amplicon with expected size was purified from agarose gel, followed by cloning in pGEM-T easy vector (Promega, WI, USA), and was sequenced to confirm the partial cDNA sequence of EH2. Gene specific primers EHRCF2, EHRCR1 (Table 1A) were designed from obtained sequence and used for rapid amplification of cDNA ends (RACE) to acquire 5' and 3' ends. The obtained amplicons were cloned and sequenced to design terminal gene specific primers EHtrF1, i.e. SEQ ID No. 11 and EHtrR1, i.e. SEQ ID No. 12 (Table 1A) for isolation of complete ORF of EH2. Amplification using ripe mango cDNA as template and the above mentioned terminal primers for EH2 was carried out with using Advantage2 polymerase mix (Clonetech, USA) and cloned into pGEM-T easy vector, transformed into *E. coli* (Top 10) cells. Finally, presence of the complete ORF of the gene encoding epoxide hydrolase 2 enzyme was confirmed by sequencing.

The obtained sequence upon in silico analysis showed presence of the complete ORF of EH spanning 957 nucleotides with 74 nucleotides long 5' and 241 nucleotides long 3' UTR regions. Homology analysis indicated SEQ ID No. 1 encoding EH had sequence identity with other genes encoding plant soluble EH2 (Tablet).

TABLE 2

Homology analysis of SEQ ID No. 1 and SEQ ID No. 3

|  | MiEH2 |
|---|---|
| ORF length (nucleotides) | 957 |
| 3' UTR length (nucleotides) | 241 |
| 5' UTR length (nucleotides) | 74 |
| Nucleotide sequence similarity | *Prunus persica* EH2 (75%) |
|  | *Arabidopsis thaliana* EH2 (71%) |
|  | *Brassica napus* EH2 (74%) |
| Insilico translated protein |  |
| Protein length (amino acids) | 318 |
| Calculated molecular weight (kDa) | 35.9 |

Example 5

Isolation of Peroxygenase cDNA

Isolation of partial gene sequence of peroxygenase from Alphonso mango was initiated by designing degenerate primers by homology based approach. Nucleotide sequences of PGX from other plant species retrieved from NCBI were aligned and degenerate primers PGX_DeF, PGX_DeR (Table 1B) were designed. Amplification was carried out using ripe cDNA as the template. The resultant amplicon with expected size was purified from agarose gel, followed by cloning in pGEM-T easy vector (Promega, WI, USA),

TABLE 1A

Terminal Primers for synthesis of full length nucleotide sequence, SEQ ID No. 1 encoding Epoxide hydrolase 2

| Primer | Class | Primer Sequence |  |
|---|---|---|---|
| MiEH2 |  |  |  |
| EH DeF1 | A | CTYTGGTAYTCVTGGCG | SEQ ID No. 7 |
| EH DeR4 | A | CCHRYCCATGGHSC | SEQ ID No. 8 |
| EHRCF2 | B | GTGGCTTCGGTGATACTGACGC | SEQ ID No. 9 |
| EHRCR1 | B | CCTGATCAGAGGCAACGACGTC | SEQ ID No. 10 |
| EHtrF1 | C | ATGGAAGATATACAGCACAGAATTGTG | SEQ ID No. 11 |
| EHtrR1 | C | TCAGAACTTCTGAAAAAAGTTGTATATG | SEQ ID No. 12 |
| EHTOPO_F1 | D | ATGGAAGATATACAGCACAGAATT | SEQ ID No. 13 |
| EHTOPO_R1 | D | GAACTTCTGAAAAAAGTTGTATATG | SEQ ID No. 14 |
| EHpBI121F1 | E | AAAAAAGGATCCATGGAAGATATACAGCACAGAATTGTG | SEQ ID No. 15 |
| EHpBI121R1 | E | AAAAAAGGATCCTCAGAACTTCTGAAAAAAGTTGTATATGTGC | SEQ ID No. 16 |
| EHRTF4 | F | CCTTGGGCCGGGAGTCAAATAAAGG | SEQ ID No. 17 |
| EHRTR4 | F | AATGGCACATCTCGCTTGAACCCAC | SEQ ID No. 18 | and was sequenced to confirm partial cDNA sequence of PGX. Gene specific primers PGX_RCF, PGX_RCR (Table 1B) were designed from obtained sequence and used for rapid amplification of cDNA ends (RACE) to acquire 5' and 3' ends. The obtained amplicons were cloned and sequenced to design terminal gene specific primers PGX_Tr_F, i.e. SEQ ID No. 23 and PGX_Tr_R, i.e. SEQ ID No. 24 (Table 1B) for isolation of complete ORF of peroxygenase. Amplification using ripe mango cDNA as template and above mentioned terminal primers for peroxygenase was carried out using Advantage2 polymerase mix (Clonetech, USA) and cloned into pGEM-T easy vector, transformed into *E. coli* (Top 10) cells. Finally, the presence of the complete ORF of the gene encoding peroxygenase enzyme was confirmed by sequencing.

TABLE 1B

Terminal Primers for synthesis of full length nucleotide sequence, SEQ ID No. 4 encoding Peroxygenase

| Primer | Class | Primer Sequence | |
|---|---|---|---|
| MiPGX1 | | | |
| PGX_De_F | A | MWGAGYGTBCTKCARCA GCATG | SEQ ID No. 19 |
| PGX_De_R | A | AMTCRAACAARCTMCCA TC | SEQ ID No. 20 |
| PGX_RC_F | B | GGGATCATTTACCCTTG GGAGAC | SEQ ID No. 21 |
| PGX_RC_R | B | CCCCTTTACTTGCAATC CAGCC | SEQ ID No. 22 |
| MiPGX_Tr_F | C | ATGGACGGGGATGCAAT GGCAACC | SEQ ID No. 23 |
| MiPGX_Tr_R | C | TTAAATCATCTTAGCTG CAGCGCCTGC | SEQ ID No. 24 |
| MiPGX1_RT_F1 | F | AAGGAAGGTACATGCCT GCAAACCT | SEQ ID No. 25 |
| MiPGX1_RT_R1 | F | CGGTTTCCCTCAGTCAT GTCCCAAA | SEQ ID No. 26 |

Example 6

Cloning and Recombinant Expression of MiEH2

The full length sequence of MiEH2 was amplified from the cDNA prepared from ripe Alphonso fruit RNA using Advantage2 polymerase mix, with terminal primers EHTOPO_F1 and EHTOPO_R1 (Table 1A). The resulting amplicon of MiEH2 was cloned in the pEXP5-CT/TOPO expression vectors. After confirming the correct orientation of the insert and presence of an uninterrupted reading frame by sequencing, recombinant plasmid of MiEH2 was transformed in BL21 (DE3) pLysS Rosetta cells for recombinant expression. Starter culture was initiated in 20 ml terrific broth (TB) comprising 100 µg ml$^{-1}$ ampicillin and was incubated at 37° C.; 180 rpm for 24 hrs. Expression culture was started with 1 TB medium inoculated with 1% final concentration of starter culture and 100 µg ml$^{-1}$ ampicillin at 37° C., 180 rpm. Expression of recombinant protein was induced by 0.2 mM IPTG at 0.6 OD$_{600}$. Post induction, expression culture was incubated at 16° C., 120 rpm for 12-14 hrs, after which cells were harvested by centrifugation and re-suspended in phosphate buffer pH 7 with 20 mM imidazole. Cells were lysed by sonication and 6xHis tagged recombinant proteins were purified on Ni-NTA matrix (Invitrogen, USA), and nonspecifically bound non-recombinant proteins were removed by low molarity imidazole containing phosphate buffer washes. Recombinant EH2 protein was eluted in phosphate buffer with 250 mM imidazole, pH 7.

Example 7

Assays for Catalytic Activity of MiEH2

MiEH2 activity assay was carried out initially in 500 µl final volume of 100 mM phosphate citrate buffer pH 7.0 at 30° C. containing 200 µM substrates viz. cis-stilbene oxide (CSO), trans-stilbene oxide (TSO) and 12(13) Epoxide of linoleic acid (12,13 EpOME). Similar activity assays were carried out with protein expressed from empty vector for confirmation of EH2 activity. Optimum pH was determined by calculating activity at varied range of pH in phosphate citrate buffer at 30° C., whereas temperature optima was determined by calculating MiEH2 activity in phosphate citrate buffer pH 7 at various temperatures. After incubation and catalytic activity of EH 2, products were extracted in chloroform:methanol (2:1); completely dried in vacuum evaporator and reconstituted in the methanol. HRMS analysis carried out by accurate mass (molecular ion) identification. Identified products from assay reaction were confirmed with mass and retention time indices of authentic standards R,R hydrobenzoin and meso hydro benzoin. Extracted compounds from CSO and TSO assay reactions were separated by water (A):methanol (B) solvent gradient, 0-1 min 80% (A)/20% (B); 1-2 min 60% (A)/40% (B); 2-4 min 40% (A)/60% (B); 4-11 min 20% (A)/80% (B); 11-16 min 0% (A)/100% (B), hold for 2 min and again back to 80% (A)/20% (B) in 3 min with 2 min hold at flow rate 500 µl min$^{-1}$. Whereas compounds from assay reactions of 12,13 EpOME were separated by water (A):methanol (B) solvent gradient, at 0 min 70% (A)/30% (B); 0-2 min 50% (A)/50% (B); 2-12 min 0% (A)/100% (B), hold for 2 min and again back to 70% (A)/30% (B) in 3 min with 2 min hold at flow rate 500 µl min$^{-1}$. Quantitative analysis of CSO and TSO assay products was done by plotting standard graph of product standards. Full scans for both programs were acquired on positive ion mode with AGC target value of 1E6, resolution of 70,000 at scan range 100-500 m/z, and maximum ion injection time (IT) of 250 ms.

TABLE 3

Biochemical characterization and enzyme kinetics of MiEH2

| | MiEH2 |
|---|---|
| Optimum temperature | 45° C. |
| Optimum pH | 8 |
| Vmax (µM min$^{-1}$mg$^{-1}$) | TSO- 1055.55 ± 55.55 |
| | CSO- 26.5252 ± 4.81 |
| Km (mM) | TSO- 0.113 ± 0.003 |
| | CSO- 0.165 ± 0.044 |
| Vmax/Km min$^{-1}$mg$^{-1}$1) | TSO- 9.336 |
| | CSO- 0.160 |

Example 8

Transient Expression of SEQ ID No. 1 in Plant Expression Vector Via Agroinfiltration The full length sequence of MiEH2, i.e. SEQ ID No. 1 was cloned in a pBI121 plant expression vector between CaMV 35S promoter and GusA gene. Terminal primers were designed (Table 1A) to clone genes at BamHI restriction site. Resulted correct oriented construct pBI121+SEQ ID No. 1 and pBI121 empty vector as control were transformed in the *Agrobacterium* GV3101 strain for transient expression studies. Separate *Agrobacterium* cultures (5 mL) were initiated from individual colonies in YEB medium having appropriate antibiotics and incubated overnight at 28° C. This culture was transferred to 50 mL induction medium comprising 0.5% beef extract, 0.1% yeast extract, 0.5% peptone, 0.5% sucrose, 2 mM MgSO4, 20 mM acetosyringone, 10 mM MES, pH 5.6, having appropriate antibiotics, and again grown overnight. Cultures were recovered by centrifugation on the next day, resuspended in infiltration medium (10 mM $MgCl_2$, 10 mM MES, 200 mM acetosyringone, pH 5.6) till optical density reached 1.0. This suspension was again incubated at 28° C. with gentle agitation for 2 hrs.

Figure 1:
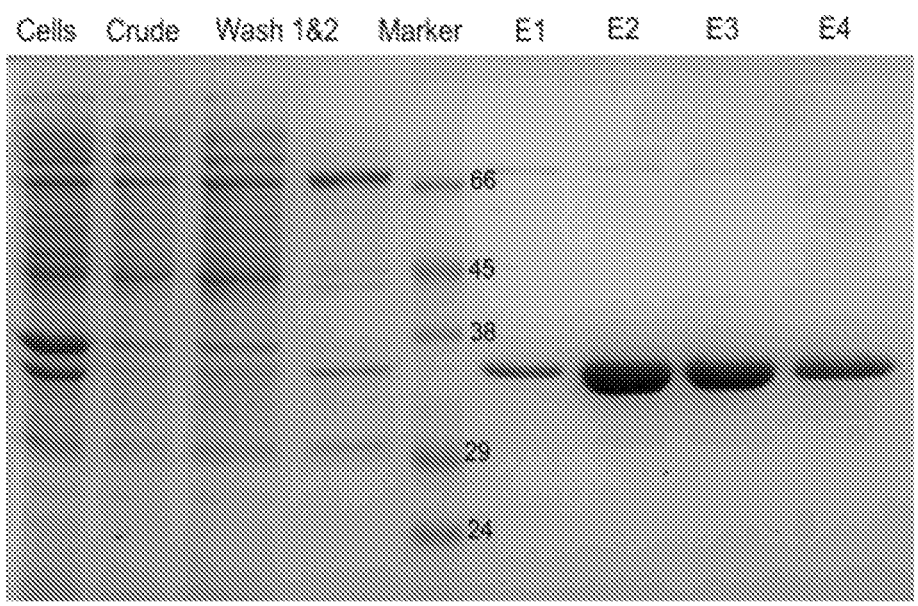
Figure 2:
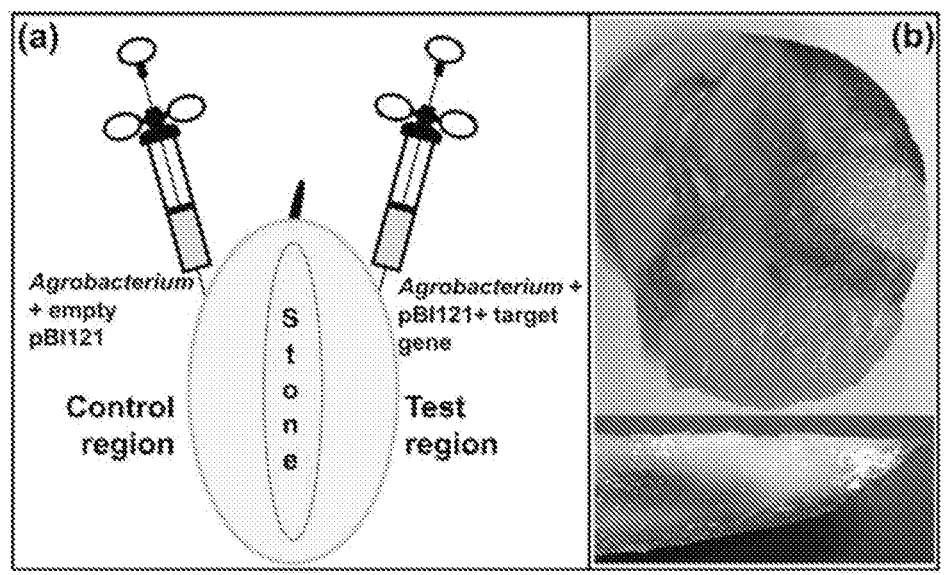
Figure 3:
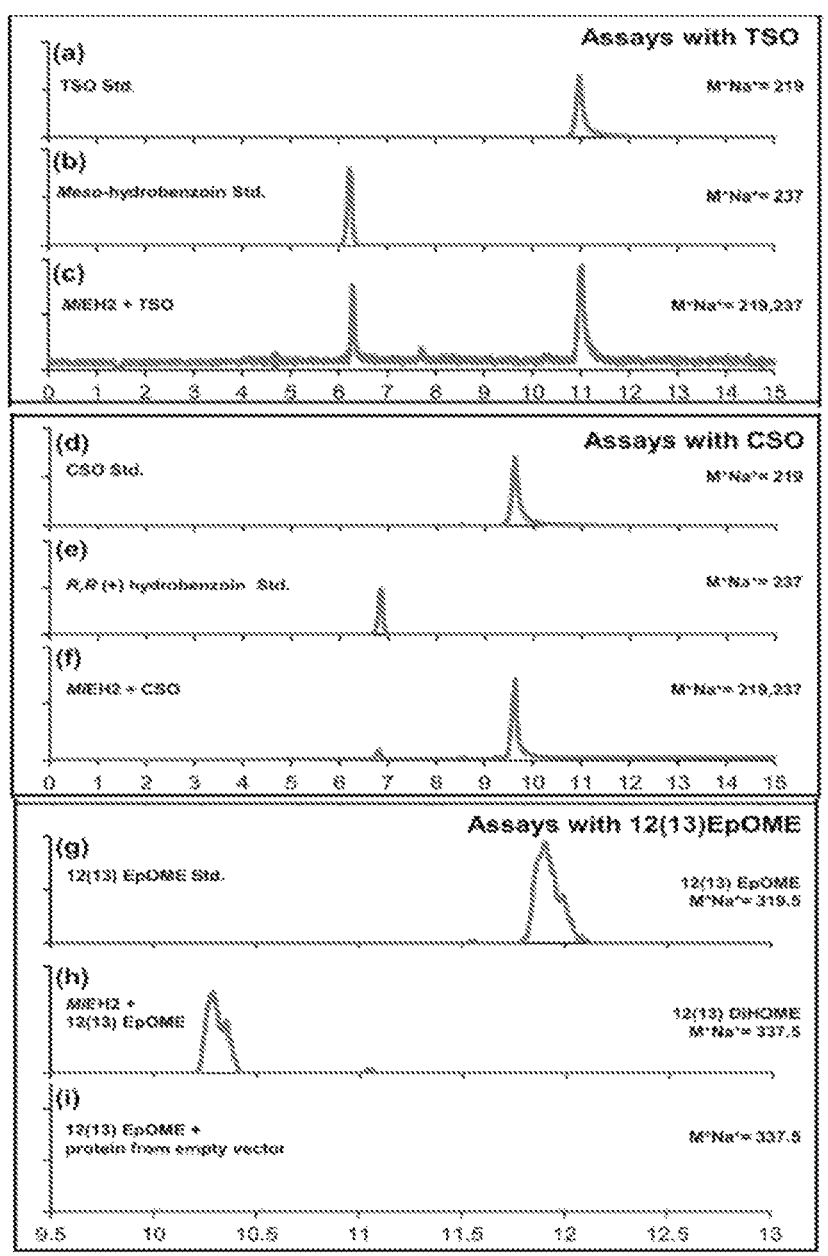
Figure 4:
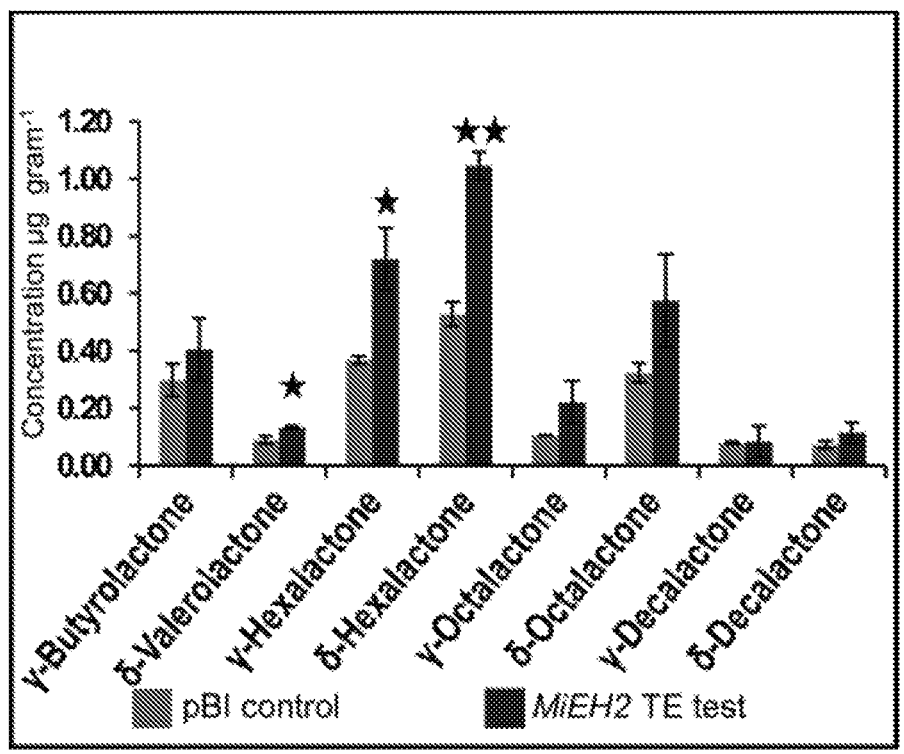
FIG. 4 shows column graphs representing changes in lactone content with respect to control upon transient over expression of MiEH2. Vertical bars represent standard error in the values of lactones from used data set, ★$p \leq 0.1$; ★★$p < 0.05$.
Figure 5:
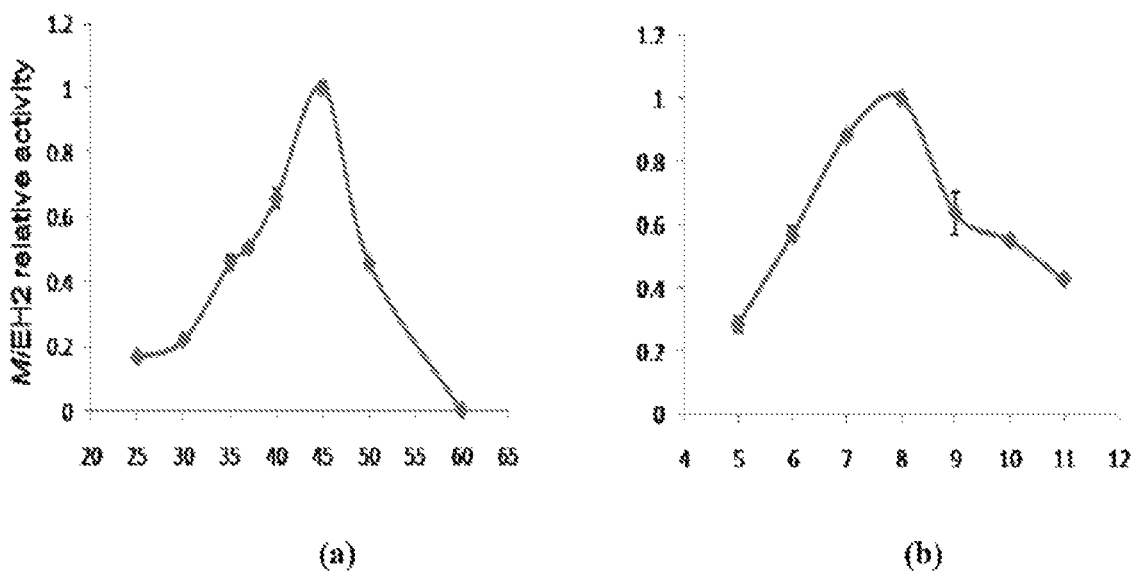
FIG. 5 depicts line graphs representing changes in the activity of MiEH2 at different pH (a) and temperatures (b)

Over expression studies for EH2 were carried out by *Agrobacterium* mediated infiltration in ethylene treated mango fruits at 3DAH stage by using hypodermic syringe. Equal volumes of said constructs i.e. pBI121+MiEH2 and pBI121 empty vector construct were used for infiltration in two different halves of same mango fruit separated by fruit stone. Earlier studies during initial trials confirmed *Agrobacterium* mediated infiltration does not spread beyond fruit stone in case of mango. Thus control (empty vector) and test over expressions were carried out in same fruit to avoid error in lactone content analysis. Five distinct mango fruits were used for overexpression study of MiEH2. Infiltrated fruits were kept at 25° C. for 2 days in 12 hr dark and 12 hr light conditions, after 2 days; part from each fruit halves was checked by Gus staining (Kapila et al. 1997; Spolaore et al. 2001) to confirm expression of MiEH2 under 35S promoter along with GusA, remaining part of fruit pulp stored in −80° C. until used for lactone analysis by gas chromatography. Similar conditions were also used for transient expression of MiPGX in a plant expression vector via agroinfiltration. Two days post infiltration a part of fruit was checked by Gus staining (FIG. 2b) to confirm expression of GusA along with SEQ ID No. 1. The remaining tissue was used for lactone content analysis. Lactones were analysed from control and test region of fruits. A total of 8 lactones viz. γ-butyrolactone, δ-valerolactone, γ-hexalactone, δ-hexalactone, γ-octalactone, γ-octalactone, γ-decalactone and δ-decalactone were detected from all tissues in GC-MS analysis. Quantitative analysis of lactones by GC-FID showed increased lactone content (FIG. 4). In case of transient expression of SEQ ID No. 1, over expression significantly increased contents of δ-valerolactone, γ-hexalactone and δ-hexalactone, this increase was 1.46, 1.96 and 1.98 folds more, respectively compared to control tissue.

Example 9

Transient Expression of SEQ ID No. 4 in Plant Expression Vector Via Agroinfiltration The full length sequence of SEQ ID No. 4 was cloned in a pBI121 plant expression vector between CaMV 35S promoter and GusA gene. Terminal primers were designed to clone gene in pBI121 vector. Resulted correct oriented construct pBI121+SEQ ID No. 4 and the empty vector as control were transformed in *Agrobacterium* GV3101 strain for transient expression. Separate *Agrobacterium* cultures (5 mL) were initiated from individual colonies in YEB medium having appropriate antibiotics and incubated overnight at 28° C. This culture was transferred to a 50 mL induction medium as described in Example 8. Cultures were recovered by centrifugation on the next day, resuspended in infiltration medium (10 mM $MgCl_2$, 10 mM MES, 200 mM acetosyringone, pH 5.6) till optical density reached 1.0. This suspension was again incubated at 28° C. with gentle agitation for 2 hrs.

Example 10

Qualitative and Quantitative Analysis of Lactones

Aroma volatile extraction was carried out from 5 g of tissues obtained from transient expression study (demonstrated in example 8) by solvent extraction method as mentioned earlier (Kulkarni et al. 2012; Pandit et al. 2009a). GC-MSD and GC-FID analysis for lactones was carried out using a 7890B GC system Agilent Technologies coupled with Agilent 5977A MSD (Agilent technologies, CA, USA). Aroma volatiles were separated on GsBP-5MS (GeneralSeparation Technologies, Newark, Del.) capillary column (30 m×0.32 mm i.d.×0.25 μm film thickness). Other chromatographic conditions were maintained as mentioned by Kulkarni et al. 2012. To understand effect of gene over expression by transient expression on lactone biosynthesis, qualitative and quantitative analysis for lactones alone was carried out in the present study. Lactones were identified by matching generated spectra with NIST 2011 and Wiley 10$^{th}$ edition mass spectral libraries. Identified compounds were confirmed by matching retention time and spectra of authentic standards procured from Sigma Aldrich (St. Louis, Mo., USA). Absolute quantification was done using internal standard by normalizing concentrations of all the lactones with that of known concentration of nonyl acetate.

Example 11

Quantitative Real-Time PCR

Quantitative real-time PCR was performed using FastStart Universal SYBR Green master mix (Roche Inc. Indianapolis, Ind., USA) and elongation factor 1α (EF1α) as an endogenous control employing the primers mentioned earlier (Pandit et al. 2010). Transcript of SEQ ID No. 1 was amplified using gene specific primers Seq. Id no. 17 and 18 (Table1A) and quantification was done by ViiA™ 7 Real-Time PCR System (Applied Biosystems, CA, USA) having thermal cycle program of initial denaturation at 95° C. for 10 min with subsequent 40 cycles of 95° C. for 3 sec and 60° C. for 30 sec followed by a dissociation curve analysis of transcripts. The analysis was carried out through pulp and skin tissues from developing and ripening stages of Alphonso, Pairi and Kent mango fruits. The expression patterns of genes from hypothesized lactone biosynthetic pathway included the isolation of full length gene sequences of peroxygenase (PGX by degenerate primer (Table 1B) approach. RACE reactions with gene specific primers (Table 1B) were carried out to obtain ends of cDNAs. Gene specific primers SEQ ID No. 25 and 26 (Table1B) were designed to carry out quantitative real time PCR. Quantitative real-time PCR analysis of peroxygenase PGX, was carried out in a similar way as that of MiEH2.

Example 12

Variable Lactone Content of Different Mango Cultivars Through RT-PCR

Transient over expression studies of SEQ ID No. 1 resulted in significant increase in the lactone content thereby confirming involvement of epoxide hydrolase 2 in lactone biosynthetic pathway in Alphonso mango. Lactone content varies amid different mango cultivars. In order to determine the role of epoxide hydrolase 2 enzyme in the lactone biosynthetic pathway fruits from low lactone containing mango cultivar Pairi and lactone less cultivar Kent along with the fruits from high lactone containing Alphonso were studied for their SEQ ID No. 1 transcripts profile through real time PCR analysis. Pulp and skin tissues from Alphonso, Pairi and Kent cultivar through various stages of fruit development and ripening were analyzed to check transcript profiles of MiPGX1, and MiEH2. The relative quantification of transcripts from Alphonso, Pairi and Kent showed ripening specific appearance of MiPGX1 (FIG. 6). In Alphonso Pulp and skin tissues optimum transcript levels of MiPGX1 were observed at mid ripe stage (10DAH stage), this finding correlates with earlier studies of the present inventor where first appearance of lactones was observed at 10 DAH stage during ripening of mango (Kulkarni et al. 2012; Pandit et al. 2009b). Similar to the Alphonso, optimum transcript levels of MiPGX1 were observed at mid ripe stage of Pairi fruit ripening.

Advantages of the Invention

The nucleotide sequences deciphered in the present invention aid in overexpression of lactones in the mangoes, thereby increasing the flavor quality in such fruits.

Transient expression of the disclosed sequences in mango via agroinfiltration results in the increased lactone concentration level in mango.

Gene specific primers employed in the present invention may be used commercially in the synthesis of the said nucleotide sequences.

We claim:

1. A recombinant polynucleotide involved in lactone synthesis in mango, wherein the polynucleotide is selected from the group consisting of:
   (a) a polynucleotide sequence as set forth in SEQ ID NO: 1 encoding a recombinant polypeptide epoxide hydrolase 2 as set forth in SEQ ID NO: 3; and
   (b) a polynucleotide sequence as set forth in SEQ ID NO: 4 encoding a recombinant polypeptide peroxygenase as set forth in SEQ ID NO: 6.

2. A process for synthesis of lactones, said process comprising:
   (a) synthesizing a polynucleotide sequence as set forth in SEQ ID NO: 4;
   (b) expressing a recombinant construct carrying said polynucleotide sequence set forth in SEQ ID NO: 4 in a host cell to obtain a recombinant polypeptide peroxygenase as set forth in SEQ ID NO: 6, wherein the host cell is selected from the group consisting of E.coli BL21 and E. coli Rosetta;
   (c) catalyzing conversion of unsaturated fatty acids to epoxy fatty acids in presence of the recombinant polypeptide peroxygenase of SEQ ID NO: 6 of (b) in the host cell to obtain epoxy fatty acids;
   (d) synthesizing a polynucleotide sequence as set forth in SEQ ID NO: 1;
   (e) expressing a recombinant construct carrying said polynucleotide sequence set forth in SEQ ID NO: 1 in the host cell to obtain recombinant epoxide hydrolase 2 as set forth in SEQ ID NO: 3;
   (f) catalyzing conversion of the epoxy fatty acids from (c) to di-hydroxy fatty acids in presence of the recombinant epoxide hydrolase 2 set forth in SEQ ID NO: 3 of (e) in the host cell to obtain di-hydroxy fatty acids; and
   (g) subjecting the di-hydroxy fatty acids of (f) to multiple cycles of ω and β oxidation in the host cell to obtain the lactones.

3. The process as claimed in claim 2, wherein said polynucleotide is a cDNA.

4. The process as claimed in claim 2, wherein the polynucleotide set forth in SEQ ID NO: 4 is synthesized by using primer pairs selected from the group consisting of SEQ ID NO: 19-SEQ ID NO: 20, SEQ ID NO: 21-SEQ ID NO: 22, SEQ ID NO: 23-SEQ ID NO: 24, and SEQ ID NO: 25-SEQ ID NO: 26.

5. The process as claimed in claim 2, wherein the polynucleotide set forth in SEQ ID NO: 1 is synthesized by using primer pairs selected from the group consisting of SEQ ID NO: 7-SEQ ID NO: 8, SEQ ID NO: 9-SEQ ID NO: 10, SEQ ID NO: 11-SEQ ID NO: 12, SEQ ID NO: 13-SEQ ID NO: 14, SEQ ID NO: 15-SEQ ID NO: 16, and SEQ ID NO: 17-SEQ ID NO: 18.

6. The process as claimed in claim 2, wherein the recombinant construct comprises:
   (i) an expression vector selected from a plant plasmid expression vector or a bacterial plasmid expression vector; and
   (ii) a polynucleotide sequence selected from the group consisting of SEQ ID NO: 1 and SEQ ID NO: 4.

7. The process as claimed in claim 6, wherein the expression vector is selected from the group consisting of pBI121, pET101D, pEXP5-CT/TOPO and pGEMT.

8. The process as claimed in claim 2, wherein the lactones are selected from the group consisting of γ-butyrolactone, δ-valerolactone, γ-hexalactone, δ-hexalactone, γ-octalactone, δ-octalactone, γ-decalactone, and δ-decalactone.

9. A process of enhancing the synthesis of lactone in fruit of a plant, wherein the method comprises introducing a recombinant construct carrying a polynucleotide sequence as set forth in SEQ ID NO: 4 and a recombinant construct carrying a polynucleotide sequence as set forth in SEQ ID NO: 1 in the fruit of the plant by agroinfiltration.

* * * * *

SEQUENCE LISTING

```
<160> NUMBER OF SEQ ID NOS: 26

<210> SEQ ID NO 1
<211> LENGTH: 957
<212> TYPE: DNA
<213> ORGANISM: Artificial Sequence
<220> FEATURE:
<223> OTHER INFORMATION: cDNA

<400> SEQUENCE: 1
atggaagata tacagcacag aattgtgaat gtcaatggct taaacatgca cgtggcagag      60
aaaggcgaag gtccagtcat tctcttcatt cacggttttc ccgaactgtg gtactcctgg     120
cggcatcaga tcatcgcctt ggcttccctc ggctaccgag ccattgctcc ggatctacgt     180
ggcttcggtg atactgacgc gccgccgtct gtctcgagtt acacgtgttt ccacgtggtg     240
ggggacctca ttggacttct cgacgtcgtt gcctctgatc gggataaggt tttcgtggtg     300
ggccatgatt ggggtgctct tattgcttgg tacttgtgct tgtttagacc ggataaggtc     360
aaagctttgg tcaacttgag tgttgcgttt aatccctgga accccaagag gaagccactt     420
gagggtttga aagctgttta tggtgacgat tattacatga tcagatttca ggagcctggt     480
gagatagaag ctgagtttgc ccagattggt actgagacag ttgtcaagga attctttaca     540
tacaggacac ctggtcctct ttttctccct acaggtaaag gatttggaca tcccccaaat     600
gctgaaattg tcttaccctc ttggctatca gaggatgatg ttaaaaacta caccagcaaa     660
tttgagaaag gctttacagg aggagtgaac tattaccgta atataaacgt gaactgggaa     720
cttacagctc cttgggccgg gagtcaaata aaggttcctg ttaagttcat cgtgggtgac     780
ctggacctga catattatat gccaggagtc aaggattaca tacacaaagg tgggttcaag     840
cgagatgtgc cattattgga agaagtgatt gtaatggaag gtgtaggtca cttcattaat     900
ggagaaaagg ctgatgcaat cagtgagcac atatacaact tttttcagaa gttctga       957

<210> SEQ ID NO 2
<211> LENGTH: 1875
<212> TYPE: DNA
<213> ORGANISM: Mangifera indica

<400> SEQUENCE: 2
atggaagata tacagcacag aattgtgaat gtcaatggct taaacatgca cgtggcagag      60
aaaggcgaag gtccagtcat tctcttcatt cacggttttc ccgaactgtg gtactcctgg     120
cggcatcaga tcatcgcctt ggcttccctc ggctaccgag ccattgctcc ggatctacgt     180
```

| | |
|---|---|
| ggcttcggtg atactgacgc gccgccgtct gtctcgagtt acacgtgttt ccacgtggtg | 240 |
| ggggacctca ttggacttct cgacgtcgtt gcctctgatc gggataaggt tttcgtggtg | 300 |
| ggccatgatt ggggtgctct tattgcttgg tacttgtgct tgtttagacc ggataaggtc | 360 |
| aaagctttgg tcaacttgag tgttgcgttt aatccctgga accccaagag gaagccactt | 420 |
| gagggtttga agctgtttta tggtgacgat tattacatga tcagatttca ggttcatttt | 480 |
| tcaacttatt ttagttttgt aattgttttt tctaactgct ttgggggttt tgcttctgct | 540 |
| gctaattaag ttatcaatga atgattgatt tgctgcaaag ttttgacctt tgatttctta | 600 |
| tttgctttga tccttgaatg tttcatcaga tctttactga acaacatga attttagcga | 660 |
| acctggaaag taggaagctc tgtatagata ttgctcgttg gtttagaatt ctactatag | 720 |
| tgctaaagct agcttttgaa atggagagtt taccgccacc tctacagcgg tgatggctca | 780 |
| ctgttagcct tgggtaaaca ctgtaaaagt tagttattga aattagaaaa tctaaaacta | 840 |
| tataaaccct aaatcaaaga ccatattttt tgatgtagaa atcaaatctc gtagcataca | 900 |
| cttggagtga taacatttca gtctgtttga agtagggttc tttgatcaca tcatcttgca | 960 |
| catgtcatag catctttaat ttgagcatgt gaaagataaa gttagaagtt tacatttatt | 1020 |
| aatcatagat tcagttgatc ttgttgccca tgaacttaaa tttttttattt gttccaaagt | 1080 |
| tttaaggcag ttctactgtc attccataac atgccagagc attttgccct gtagctggag | 1140 |
| gttctacatc aattcattta ctgatgaata tcaatcatag agcacaattt cgcattttga | 1200 |
| taaaatcaaa atagctcacc taatgaaccg attgcttgac gggattgtag gagcctggtg | 1260 |
| agatagaagc tgagtttgcc cagattggta ctgagacagt tgtcaaggaa ttctttacat | 1320 |
| acaggacacc tggtcctctt tttctcccta caggtaaagg attggacat cccccaaatg | 1380 |
| ctgaaattgt cttaccctct tggctatcag aggatgatgt taaaaactac accagcaaat | 1440 |
| ttgagaaagg ctttacagga gggagtgaact attaccgtaa tataaacgtg tatgtctcct | 1500 |
| tccaagtcat atgagcagct atatctgttt tgcttgatcc aatctggcat gaatttgatt | 1560 |
| atctagtggt gatcttttac tcaattatat ggcattgtca ctcatgttta ctctcctttt | 1620 |
| tgctgcagga actgggaact tacagctcct tgggccggga gtcaaataaa ggttcctgtt | 1680 |
| aagttcatcg tgggtgacct ggacctgaca tattatatgc caggaaggaa ggattacata | 1740 |
| cacaaaggtg ggttcaagcg agatgtgcca ttattggaag aagtgattgt aatgaaggt | 1800 |
| gtaggtcact tcattaatgg agaaaggct gatgcaatca gtgagcacat atacaacttt | 1860 |
| tttcagaagt tctga | 1875 |

<210> SEQ ID NO 3
<211> LENGTH: 318
<212> TYPE: PRT
<213> ORGANISM: Mangifera indica

<400> SEQUENCE: 3

Met Glu Asp Ile Gln His Arg Ile Val Asn Val Asn Gly Leu Asn Met
1               5                   10                  15

His Val Ala Glu Lys Gly Glu Gly Pro Val Ile Leu Phe Ile His Gly
            20                  25                  30

Phe Pro Glu Leu Trp Tyr Ser Trp Arg His Gln Ile Ile Ala Leu Ala
        35                  40                  45

Ser Leu Gly Tyr Arg Ala Ile Ala Pro Asp Leu Arg Gly Phe Gly Asp
    50                  55                  60

Thr Asp Ala Pro Pro Ser Val Ser Ser Tyr Thr Cys Phe His Val Val
65                  70                  75                  80

Gly Asp Leu Ile Gly Leu Leu Asp Val Val Ala Ser Asp Arg Asp Lys
            85                  90                  95

Val Phe Val Val Gly His Asp Trp Gly Ala Leu Ile Ala Trp Tyr Leu
            100                 105                 110

Cys Leu Phe Arg Pro Asp Lys Val Lys Ala Leu Val Asn Leu Ser Val
            115                 120                 125

Ala Phe Asn Pro Trp Asn Pro Lys Arg Lys Pro Leu Glu Gly Leu Lys
    130                 135                 140

Ala Val Tyr Gly Asp Asp Tyr Tyr Met Ile Arg Phe Gln Glu Pro Gly
145                 150                 155                 160

Glu Ile Glu Ala Glu Phe Ala Gln Ile Gly Thr Glu Thr Val Val Lys
                165                 170                 175

Glu Phe Phe Thr Tyr Arg Thr Pro Gly Pro Leu Phe Leu Pro Thr Gly
            180                 185                 190

Lys Gly Phe Gly His Pro Pro Asn Ala Glu Ile Val Leu Pro Ser Trp
            195                 200                 205

Leu Ser Glu Asp Asp Val Lys Asn Tyr Thr Ser Lys Phe Glu Lys Gly
210                 215                 220

Phe Thr Gly Gly Val Asn Tyr Tyr Arg Asn Ile Asn Val Asn Trp Glu
225                 230                 235                 240

Leu Thr Ala Pro Trp Ala Gly Ser Gln Ile Lys Val Pro Val Lys Phe
                245                 250                 255

Ile Val Gly Asp Leu Asp Leu Thr Tyr Tyr Met Pro Gly Val Lys Asp
            260                 265                 270

Tyr Ile His Lys Gly Gly Phe Lys Arg Asp Val Pro Leu Leu Glu Glu
            275                 280                 285

Val Ile Val Met Glu Gly Val Gly His Phe Ile Asn Gly Glu Lys Ala
            290                 295                 300

Asp Ala Ile Ser Glu His Ile Tyr Asn Phe Phe Gln Lys Phe
305                 310                 315

<210> SEQ ID NO 4
<211> LENGTH: 708
<212> TYPE: DNA
<213> ORGANISM: Artificial Sequence
<220> FEATURE:
<223> OTHER INFORMATION: cDNA sequence encoding peroxygenase

<400> SEQUENCE: 4
atggacgggg atgcaatggc aaccgaggct ccttatgcac cagtcactta tgagagaaga      60
gtccccactg acttggatga caaaattccc aagcctttata tgccaagagc actggaagct     120
ccagatccga gccatccaaa tggaacacaa gggcacaata atcacaacct gagtgtgctt     180
cagcagcatg tagccttttt tgaccaagat gacaatggga tcatttaccc ttgggagact     240
tatacaggac taagagcaat tggtttcaac atgatagttt ctgtgatatt ggcctttgtc     300
atcaacttgg cactgagtta tcctactctc cccggggtgga tcccatctcc tttcttaccc     360
atttacatac acaacataca caaagcaaag catggcagtg actcaggaac atatgacacg     420
gaaggaaggt acatgcctgc aaacctggaa ttcatattta gcaaatattc tcatacagtg     480
cctggtaagt taacaatagg agagctttgg gacatgactg agggaaaccg tgtagcaatg     540
gacttctttg ctggattgc aagtaaaggg gaatggcttg ttttatacat tttggcgagg     600
gacgaggaag gtttcctatc aaaagaagct gtgagacgct gttacgatgg tagtttgttt     660

```
gagtactgtg caaaactgaa tgcaggcgct gcagctaaga tgatttaa            708
```

<210> SEQ ID NO 5
<211> LENGTH: 1515
<212> TYPE: DNA
<213> ORGANISM: Mangifera indica

<400> SEQUENCE: 5

```
atggacgggg atgcaatggc aaccgaggct ccttatgcac cagtcactta tgagagaaga    60
gtccccactg acttggatga caaaattccc aagccttgta tgcttttcg cttccatttc    120
cactgctcta tttattattt attttaatc ataaattgta acatatctag gcaaatccta    180
tttggacaaa atataggaga gatctcttat gttttgtgta tatatgaata ttccataccg    240
ttgaaaatgt taaaaagat tgtttatctt aagttcttta aaaaagactg attattatgg    300
atatcttgga aaaaaaaaa agacaaacct tattgtctta tacatgtcaa gaagatatgt    360
tttatatgta tgaacatctc atatgaatga taaaatggtt gaataatgtt ctaaattata    420
gagatgtctg atagactata tttaaagtag ataatgtcat aatagtggac taagttatta    480
aactagaata ttcataaat caaccattat gacagaatag taggagaaaa aaaagataaa    540
tcttattgtt aagttggttt ctagattgta aatttgtgag aaaattaagc tgtaaatttt    600
attcgatctg tctgatttat gttcaactta gatatgccaa gagcactgga agctccagat    660
ccgagccatc caaatggaac acaagggcac aataatcaca acctgagtgt gcttcagcag    720
catgtagcct tttttgacca agatgacaat gggatcattt acccttggga gacttataca    780
ggactaagag caattggttt caacatgata gtttctgtga tattggcctt tgtcatcaac    840
ttggcactga gttatcctac tctccccggg tggatcccat ctccttctt acccattac    900
atacacaaca tacacaaagc aaagcatggc agtgactcag gaacatatga cacggaagga    960
aggtacatgc ctgcaaacct ggaattcata tttagcaaat attctcatac agtgcctggt    1020
aagttaacaa taggagagct ttgggacatg actgagggaa accgtgtagc aatggacttc    1080
tttggctggt aagttgttaa tcaatgttgt atagctagtt tcagtagttg gatcactatg    1140
aaaatatggg ctgtgaaatt aaaacacctc ttaacttcac aatctattta agtaatcttg    1200
aatatttat atatatct aacatctttc ccatattttg taaatgtaaa atttgtttaa    1260
aactattaca aacgcaccca tttcaatgaa ttgaactgtc attttaact taaagaaat    1320
gcactgaata agagtaaggg ttggttgcat atggattgca ggattgcaag taaggggaa    1380
tggcttgttt tatacatttt ggcgagggac gaggaaggtt tcctatcaaa agaagctgtg    1440
agacgctgtt acgatggtag tttgtttgag tactgtgcaa aactgaatgc aggcgctgca    1500
gctaagatga tttaa                                                      1515
```

<210> SEQ ID NO 6
<211> LENGTH: 235
<212> TYPE: PRT
<213> ORGANISM: Mangifera indica

<400> SEQUENCE: 6

```
Met Asp Gly Asp Ala Met Ala Thr Glu Ala Pro Tyr Ala Pro Val Thr
 1               5                  10                  15

Tyr Glu Arg Arg Val Pro Thr Asp Leu Asp Asp Lys Ile Pro Lys Pro
            20                  25                  30

Tyr Met Pro Arg Ala Leu Glu Ala Pro Asp Pro Ser His Pro Asn Gly
        35                  40                  45
```

-continued

```
Thr Gln Gly His Asn Asn His Asn Leu Ser Val Leu Gln Gln His Val
 50                  55                  60

Ala Phe Phe Asp Gln Asp Asn Gly Ile Ile Tyr Pro Trp Glu Thr
 65                  70                  75                  80

Tyr Thr Gly Leu Arg Ala Ile Gly Phe Asn Met Ile Val Ser Val Ile
                 85                  90                  95

Leu Ala Phe Val Ile Asn Leu Ala Leu Ser Tyr Pro Thr Leu Pro Gly
                100                 105                 110

Trp Ile Pro Ser Pro Phe Leu Pro Ile Tyr Ile His Asn Ile His Lys
            115                 120                 125

Ala Lys His Gly Ser Asp Ser Gly Thr Tyr Asp Thr Glu Gly Arg Tyr
        130                 135                 140

Met Pro Ala Asn Leu Glu Phe Ile Phe Ser Lys Tyr Ser His Thr Val
145                 150                 155                 160

Pro Gly Lys Leu Thr Ile Gly Glu Leu Trp Asp Met Thr Glu Gly Asn
                165                 170                 175

Arg Val Ala Met Asp Phe Phe Gly Trp Ile Ala Ser Lys Gly Glu Trp
                180                 185                 190

Leu Val Leu Tyr Ile Leu Ala Arg Asp Glu Glu Gly Phe Leu Ser Lys
            195                 200                 205

Glu Ala Val Arg Arg Cys Tyr Asp Gly Ser Leu Phe Glu Tyr Cys Ala
        210                 215                 220

Lys Leu Asn Ala Gly Ala Ala Ala Lys Met Ile
225                 230                 235

<210> SEQ ID NO 7
<211> LENGTH: 17
<212> TYPE: DNA
<213> ORGANISM: Artificial Sequence
<220> FEATURE:
<223> OTHER INFORMATION: EH DeF1primer

<400> SEQUENCE: 7
ctytggtayt cvtggcg                                                17

<210> SEQ ID NO 8
<211> LENGTH: 14
<212> TYPE: DNA
<213> ORGANISM: Artificial Sequence
<220> FEATURE:
<223> OTHER INFORMATION: EH DeR4 primer

<400> SEQUENCE: 8
cchryccatg ghsc                                                   14

<210> SEQ ID NO 9
<211> LENGTH: 22
<212> TYPE: DNA
<213> ORGANISM: Artificial Sequence
<220> FEATURE:
<223> OTHER INFORMATION: EHRCF2 primer

<400> SEQUENCE: 9
gtggcttcgg tgatactgac gc                                          22

<210> SEQ ID NO 10
<211> LENGTH: 22
<212> TYPE: DNA
<213> ORGANISM: Artificial Sequence
<220> FEATURE:
```

<223> OTHER INFORMATION: EHRCR1 primer

<400> SEQUENCE: 10
cctgatcaga ggcaacgacg tc                                    22

<210> SEQ ID NO 11
<211> LENGTH: 27
<212> TYPE: DNA
<213> ORGANISM: Artificial Sequence
<220> FEATURE:
<223> OTHER INFORMATION: EHtrF1 primer

<400> SEQUENCE: 11
atggaagata tacagcacag aattgtg                               27

<210> SEQ ID NO 12
<211> LENGTH: 28
<212> TYPE: DNA
<213> ORGANISM: Artificial Sequence
<220> FEATURE:
<223> OTHER INFORMATION: EHtrR1 primer

<400> SEQUENCE: 12
tcagaacttc tgaaaaaagt tgtatatg                              28

<210> SEQ ID NO 13
<211> LENGTH: 24
<212> TYPE: DNA
<213> ORGANISM: Artificial Sequence
<220> FEATURE:
<223> OTHER INFORMATION: EHTOPO_F1 primer

<400> SEQUENCE: 13
atggaagata tacagcacag aatt                                  24

<210> SEQ ID NO 14
<211> LENGTH: 26
<212> TYPE: DNA
<213> ORGANISM: Artificial Sequence
<220> FEATURE:
<223> OTHER INFORMATION: EHTOPO_R1 primer

<400> SEQUENCE: 14
gaacttctga aaaagttgt tatatg                                 26

<210> SEQ ID NO 15
<211> LENGTH: 39
<212> TYPE: DNA
<213> ORGANISM: Artificial Sequence
<220> FEATURE:
<223> OTHER INFORMATION: EHpBI121F1 primer

<400> SEQUENCE: 15
aaaaaaggat ccatggaaga tatacagcac agaattgtg                  39

<210> SEQ ID NO 16
<211> LENGTH: 43
<212> TYPE: DNA
<213> ORGANISM: Artificial Sequence
<220> FEATURE:
<223> OTHER INFORMATION: EHpBI121R1 primer

<400> SEQUENCE: 16
aaaaaaggat cctcagaact tctgaaaaaa gttgtatatg tgc             43

<210> SEQ ID NO 17
<211> LENGTH: 25
<212> TYPE: DNA
<213> ORGANISM: Artificial Sequence
<220> FEATURE:
<223> OTHER INFORMATION: EHRTF4 primer

<400> SEQUENCE: 17
ccttgggccg ggagtcaaat aaagg             25

<210> SEQ ID NO 18
<211> LENGTH: 25
<212> TYPE: DNA
<213> ORGANISM: Artificial Sequence
<220> FEATURE:
<223> OTHER INFORMATION: EHRTR4 primer

<400> SEQUENCE: 18
aatggcacat ctcgcttgaa cccac             25

<210> SEQ ID NO 19
<211> LENGTH: 22
<212> TYPE: DNA
<213> ORGANISM: Artificial Sequence
<220> FEATURE:
<223> OTHER INFORMATION: PGX_De_F primer

<400> SEQUENCE: 19
mwgagygtbc tkcarcagca tg                22

<210> SEQ ID NO 20
<211> LENGTH: 19
<212> TYPE: DNA
<213> ORGANISM: Artificial Sequence
<220> FEATURE:
<223> OTHER INFORMATION: PGX_De_R primer

<400> SEQUENCE: 20
amtcraacaa rctmccatc                    19

<210> SEQ ID NO 21
<211> LENGTH: 23
<212> TYPE: DNA
<213> ORGANISM: Artificial Sequence
<220> FEATURE:
<223> OTHER INFORMATION: PGX_RC_F primer

<400> SEQUENCE: 21
gggatcattt acccttggga gac               23

<210> SEQ ID NO 22
<211> LENGTH: 22
<212> TYPE: DNA
<213> ORGANISM: Artificial Sequence
<220> FEATURE:
<223> OTHER INFORMATION: PGX_RC_R primer

<400> SEQUENCE: 22
cccctttact tgcaatccag cc                22

<210> SEQ ID NO 23
<211> LENGTH: 24
<212> TYPE: DNA
<213> ORGANISM: Artificial Sequence
<220> FEATURE:
<223> OTHER INFORMATION: MiPGX_Tr_F primer

```
<400> SEQUENCE: 23
atggacgggg atgcaatggc aacc                                      24

<210> SEQ ID NO 24
<211> LENGTH: 27
<212> TYPE: DNA
<213> ORGANISM: Artificial Sequence
<220> FEATURE:
<223> OTHER INFORMATION: MiPGX_Tr_R primer

<400> SEQUENCE: 24
ttaaatcatc ttagctgcag cgcctgc                                   27

<210> SEQ ID NO 25
<211> LENGTH: 25
<212> TYPE: DNA
<213> ORGANISM: Artificial Sequence
<220> FEATURE:
<223> OTHER INFORMATION: MiPGX1_RT_F1 primer

<400> SEQUENCE: 25
aaggaaggta catgcctgca aacct                                     25

<210> SEQ ID NO 26
<211> LENGTH: 25
<212> TYPE: DNA
<213> ORGANISM: Artificial Sequence
<220> FEATURE:
<223> OTHER INFORMATION: MiPGX1_RT_R1 primer

<400> SEQUENCE: 26
cggtttccct cagtcatgtc ccaaa                                     25
```